United States Patent [19]

Turner et al.

[11] 4,403,618
[45] Sep. 13, 1983

[54] APPARATUS FOR ELECTROMAGNETIC RADIATION OF LIVING TISSUE AND THE LIKE

[75] Inventors: Paul F. Turner, North Salt Lake; Om P. Gandhi, Holladay, both of Utah

[73] Assignee: BSD Medical Inc., Salt Lake City, Utah

[21] Appl. No.: 256,019

[22] Filed: Apr. 21, 1981

Related U.S. Application Data

[62] Division of Ser. No. 2,584, Jan. 11, 1979, Pat. No. 4,271,848.

[51] Int. Cl.³ ............................................. A61N 1/40
[52] U.S. Cl. .................................................. 128/804
[58] Field of Search ........................ 128/804, 802, 422

[56] References Cited

U.S. PATENT DOCUMENTS

| | | | |
|---|---|---|---|
| 1,889,272 | 11/1932 | Zerne | 128/802 |
| 2,583,853 | 1/1952 | Kazdin | 128/804 |
| 4,140,130 | 2/1979 | Storm | 128/804 |
| 4,186,729 | 2/1980 | Harrison | 128/804 |
| 4,197,860 | 4/1980 | Sterzer | 128/804 |

Primary Examiner—William E. Kamm
Attorney, Agent, or Firm—Hubbard, Thurman, Turner & Tucker

[57] ABSTRACT

Apparatus for electromagnetic radiation of living tissue, such as human tissue, or tissue simulating matter, comprises an electromagnetic radiation source having a dynamic frequency range of at least about 5 to 1, and preferably 10 to 1. Electrically connected to the source by a coaxial cable is a broadband applicator adapted for emitting electromagnetic radiation into tissue and the like. Parallel plate type radiation launching portions of the applicator are configured to have a characteristic impedance, throughout the dynamic frequency range, approximately equal to the impedance of specimens to be irradiated, which for human tissue, between 50 MHz - 2000 MHz, is approximately 50 ohms. A transition for interconnecting the coaxial cable to the parallel plate launching portion is configured to provide a relatively gradual coaxial to parallel plate transition at constant characteristic impedance throughout the dynamic frequency range. Both air filled and dielectric filled transitions and air filled, whole body and dielectric filled, partial body applicators are described.

1 Claim, 14 Drawing Figures

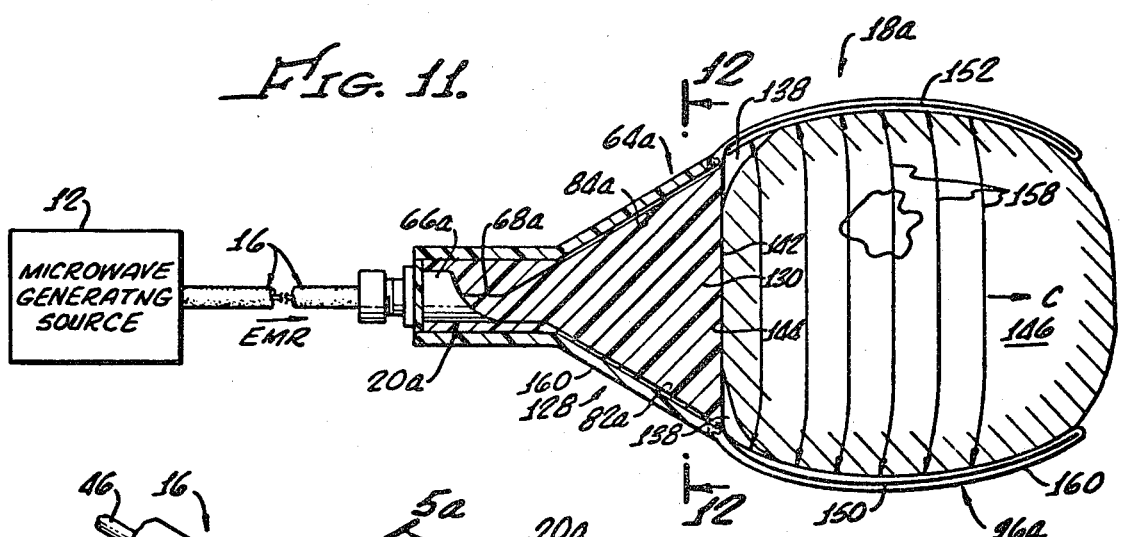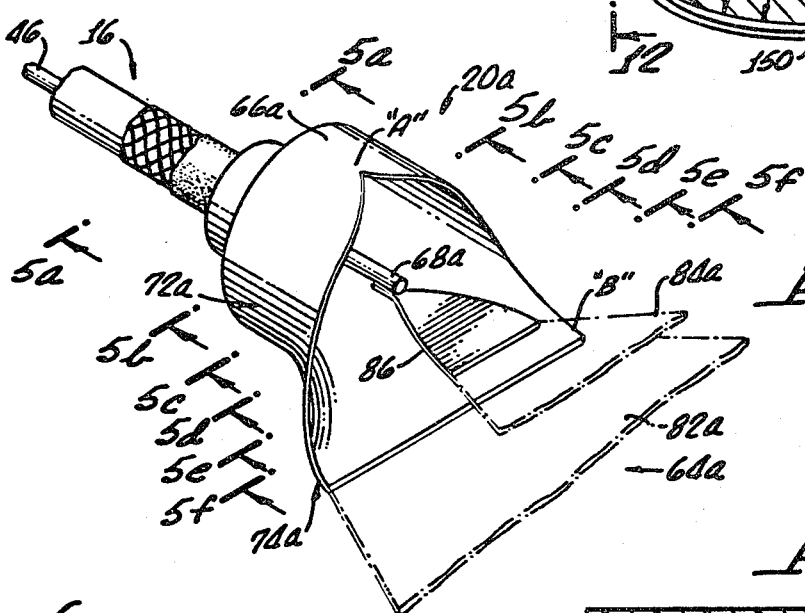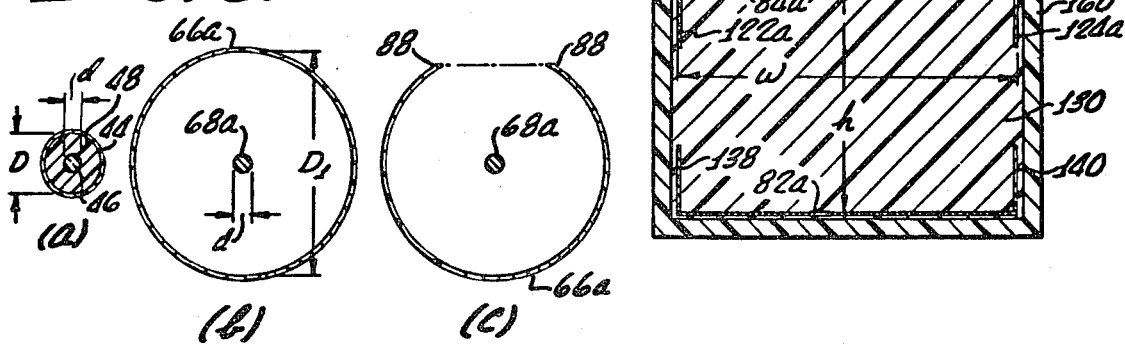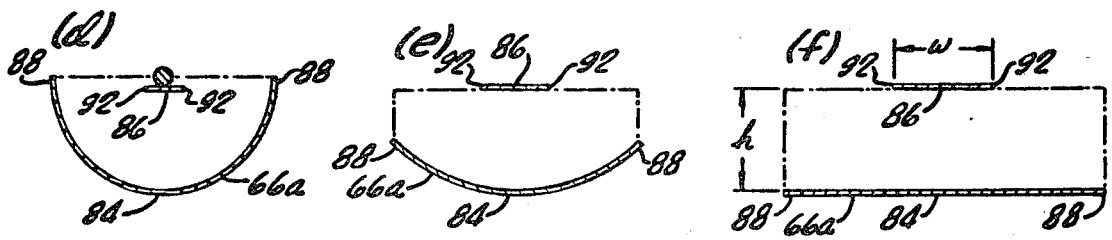

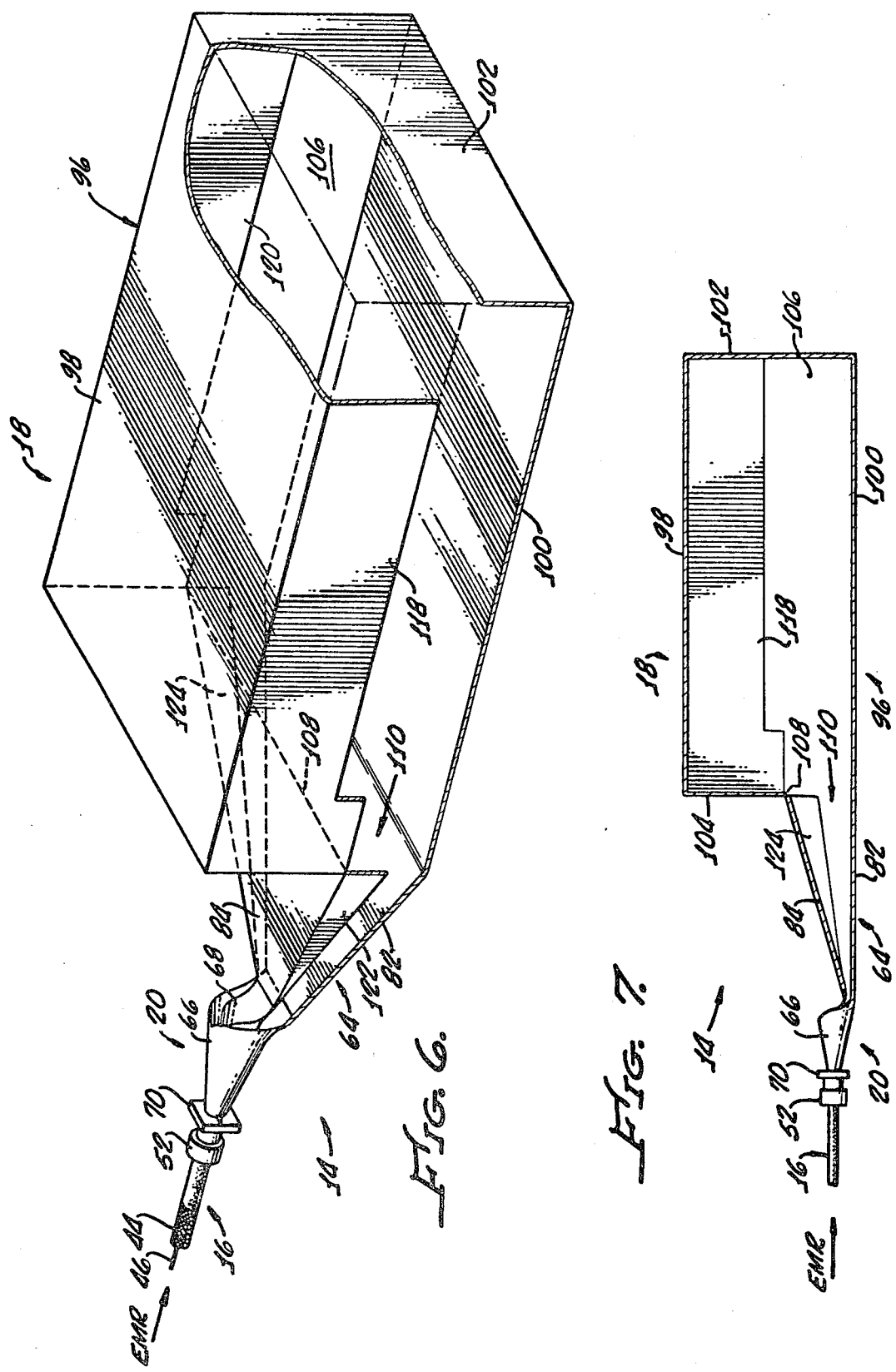

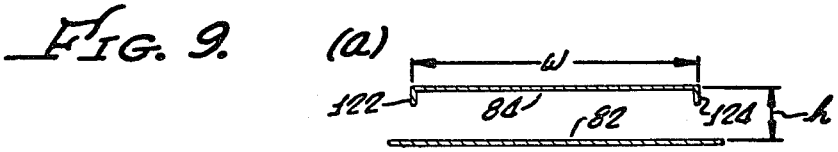
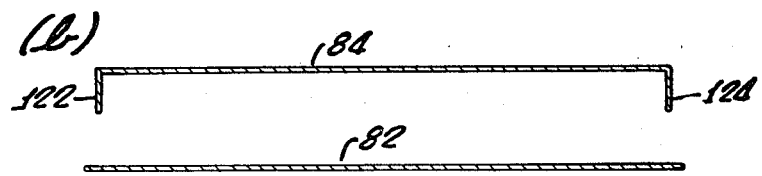
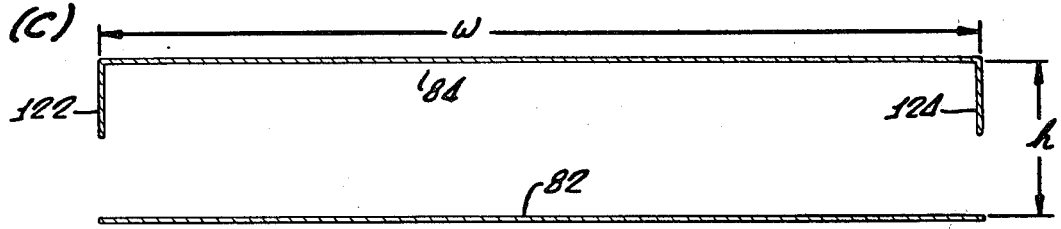
Fig. 9.
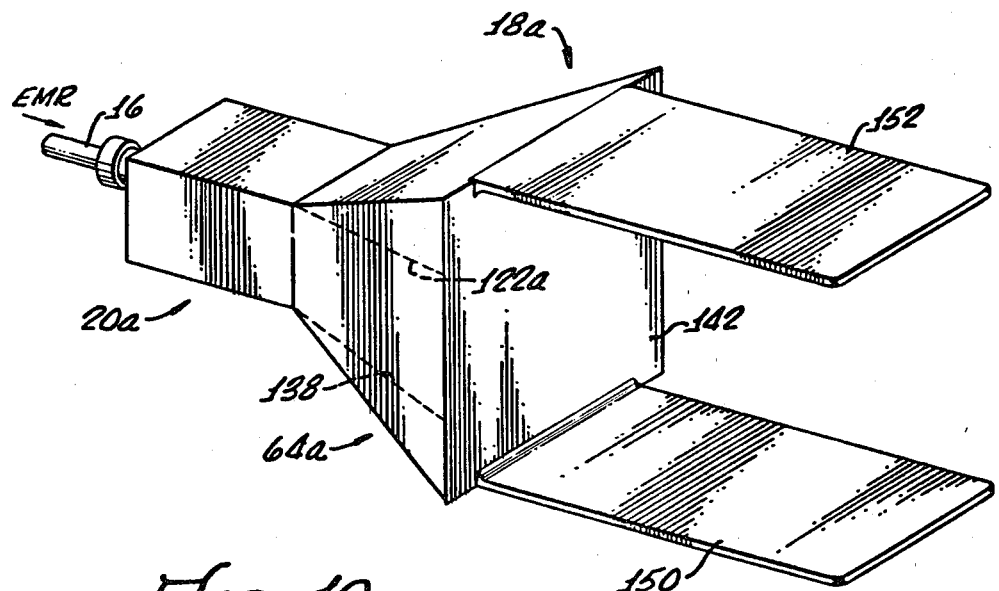
Fig. 10.

APPARATUS FOR ELECTROMAGNETIC RADIATION OF LIVING TISSUE AND THE LIKE

This application is a division, of application Ser. No. 002,584, filed Jan. 11, 1979, now U.S. Pat. No. 4,271,848.

The present invention relates generally to the field of apparatus for applying electromagnetic radiation to human and animal tissue, and more particularly to broadband systems and transmission and applicator portions of such systems adapted for medical use, for example for electromagnetic radiation hyperthermia.

Hyperthermia or induced high body temperature in general has, for many years, been of considerable interest for treating cancer, as well as various other human diseases. Some types of malignant cells reportedly can be destroyed by raising their temperatures to levels slightly below those injurious to most normal cells; hence, selective hyperthermia is possible and is an area of continuing research. Also, some types of malignant cell masses lend themselves to selective hyperthermia treatment because the masses of such malignant cells have much poorer heat dissipation characteristics than normal tissue (possibly due to poorer blood circulation therethrough), and hence can often be raised to temperatures substantially above that of surrounding healthy cells even when both are exposed to the same heat source.

Certain types of malignant cells are generally considered to have a relatively narrow thermal treatment temperature range. For example, it is believed that below a threshold of about 41.5° C. (106.7° F.) insubstantial thermal destruction of certain malignant masses occurs. At hyperthermia temperatures below this 41.5° C. threshold, growth of some malignancies may actually be stimulated. At temperatures above about 43° C. to 45° C. (109.4° F. to 113° F.) thermal damage to most normal cells is known to occur. Of course, the time exposure to the particular elevated temperature is also determinative. If large or critical portions of the body are heated into or above the 43° C. to 45° C. temperature range for too long a time, serious permanent injury or death is possible.

Although some skin malignancies have been successfully treated by application of surface heat, due to body heat transfer properties, deeply located malignant growths can rarely be heated to the necrosis temperature in this manner without causing thermal damage to overlying normal tissue.

A promising alternate hyperthermia technique is electromagnetic radiation (EMR) heating. Alternative electric currents at frequencies higher than about 10 KHz were found in the late nineteenth century to produce heating in human tissue, and were used to treat such disorders as diseased tissue and damaged muscles. In the early twentieth century the term "diathermy" was introduced to describe such tissue heating by conversion of high frequency electric currents into heat.

In 1933 hyperthermia treatment of malignant growths by high frequency EMR was described by Dr. Schereschewsky in an article entitled "Biological Effects of Very High Frequency Electromagnetic Radiation" which appeared in *RADIOLOGY* in April of that year. Experimental EMR treatment of tumors in mice at frequencies up to 300 MHz was reported and a review of activity in the EMR diathermia/hyperthermia field was presented.

More recently, in 1974, Guy, Lehman and Stonebridge presented a historical background of high frequency EMR hyperthermia and discussed current experimental activity in the field in an article entitled "Therapeutic Applications of Electromagnetic Power", appearing in the *PROCEEDINGS OF THE IEEE*, Volume 62, No. 1, January, 1974.

A serious problem associated with EMR hyperthermia has, however, been causing thermal necrosis of malignancies without excessively thermally damaging adjacent healthy tissue, for example, by excessive EMR intensity or improper frequencies, or by standing waves resulting from applied EMR energy reflections at boundaries between body tissue layers.

Still requiring further definition and investigation are potentially harmful, low level, nonthermal EMR effects, considered to be caused by electromagnetic forces acting on cell molecules, include realignment of cell molecules into chain-like formations, tendency to coagulate cell molecules, and possibly damage to normal cells resulting in a cause of cancer, and in a myriad of other physiological effects.

Low level EMR has been observed to cause effects on central nervous and cardiovascular systems, such as decreased arterial pressure and reduced heart rate, the Soviets reporting such effects at radiation levels below 10 milliwatts per square centimeter. A more thorough discussion of these nonthermal effects is, for example, presented in an article by Johnson and Guy, entitled "Nonionizing Effects of Electromagnetic Wave Effects in Biological Materials and Systems" appearing in the *PROCEEDINGS OF THE IEEE*, Volume 60, No. 6, June, 1972.

Because of these potentially harmful and/or poorly understood nonthermal EMR effects, a maximum power density for prolonged EMR exposure has been set at 10 milliwatts per square centimeter in the United States; whereas, the Soviets have established a maximum of 0.01 milliwatt per square centimeter. In contrast, EMR hyperthermia and diathermy commonly use power densities as high as one watt per square centimeter, emphasizing necessity for more research in nonthermal EMR effects.

A serious problem in EMR hyperthermia research has, at least until recently, been lack of convenient, non-interfering apparatus for accurately monitoring tissue temperature during irradiation. Conventional thermocouples typically have caused reflections of the applied radiation, resulting in hot spots at unpredictable locations. And, because the incident EMR tends to bias the thermocouples, temperature readings have been suspected as being inaccurate.

Other substantial problems have been caused by available EMR research apparatus being relatively inefficient, costly and inflexible. Typically, such apparatus has heretofore included ad hoc interconnections of standard components, such as EMR generators and transmission lines of the type generally used in microwave communications, to applicators analogous to free space radiating antenna. In consequence, mismatch of characteristic impedances ($Z_o$) at various interfaces has caused radiation reflections limiting EMR system efficiency. Accordingly, the EMR source must ordinarily provide EMR power many times higher than the power actually to be applied to the specimens to be irradiated. Although the resulting power loss may only be a few hundred watts, considerably more costly EMR sources are required than would be necessary for efficient systems.

More importantly, much of the power lost is typically radiated into the surroundings from the transmission lines and applicators. Unless extensive shielding, which restricts access to the apparatus is provided, researchers are subjected to potentially harmful levels of stray electromagnetic radiation.

When such EMR systems use only a single EMR frequency, or a very narrow range of frequencies, efficiency can be somewhat increased by compensating for impedance mismatches with "tuners". These tuners, while protecting the EMR source and increasing efficiency, however, cause standing waves in the system which in turn tends to increase radiation leakage near the radiating device.

However, for effective EMR studies using different geometric and compositions of test bodies and for investigations involving tissues heating and nonthermal effects at different depths and over different body areas, capability for radiating at frequencies over a broad dynamic range of at least about 5 to 1 and preferably 10 to 1 is desirable. Although federal limitations has been placed on diathermy frequencies which can be used, to prevent interference with broadcasting and communications, because of the different manner of applying radiation in hyperthermia use, a chamber to prevent stray interference could be used.

Other problems have been associated with EMR applicators which have typically provided poor EMR coupling into the test bodies. In addition to causing undesirable amounts of stray radiation, uniform or other specifically profiled EMR fields have been difficult to attain, and the applicators have not had good broadband capabilities. As a result, tissue heating has generally been difficult to control and predict.

The present invention provides an irradiation system combination, as well as separately useful components thereof, particularly adapted to medical research, for example, in EMR hyperthermia, while providing efficient operation throughout a broad frequency range and avoiding some of the limitations of prior systems. Included in the apparatus of the present invention are efficient EMR applicators of both whole body and localized heating types. This apparatus also has important uses in various fields of EMR irradiation research and application, including investigation of and possible ultimate use for various types of diseases and disorders, elevation of body temperature following hypothermia conditions such as low temperature operations, and investigation of nonthermal EMR irradiation effects on human and animal tissue.

In accordance with the present invention, a broadband electromagnetic radiation system particularly adapted for irradiating living tissue and tissue simulating matter comprises the following: A broadband electromagnetic radiation source having an output impedance substantially equal to an average impedance of the living tissue, or tissue simulating matter to be irradiated, over a selected dynamic frequency range of at least about 5 to 1 is coupled to a transmission means also having a characteristic impedance approximately equal to the impedance of the tissue or tissue simulating matter throughout the dynamic frequency range. An applicator for radiating, electromagnetic energy includes parallel plate-type launching means. The launching means has a characteristic impedance, when the applicator in operative relationship with tissue or tissue simulating matter for irradiation thereof, approximately equal to the average impedance of the tissue or tissue simulating matter throughout the frequency range. Electrically interconnecting the transmission means with the applicator are broadband transition means for enabling substantially reflectionless transmission, throughout the dynamic frequency range, of electromagnetic waves from the transmission means to the applicator. The transition means is configured for having a characteristic impedance approximately equal to the tissue and tissue simulating matter impedance throughout the frequency range.

Because impedances of system components are substantially matched throughout the entire dynamic frequency range, broadband operation at good efficiencies is enabled, as is important to limit radiation leakage and provide a comparatively economical system particularly adapted for research into electromagnetic radiation hyperthermia effects on living tissue and other related, medically oriented fields.

In accordance with one embodiment of the invention, the transition element, which is also a separately useful component, is configured to provide a substantially continuous transition between conventional coaxial cable, and parallel plate type transmission lines. The source end of the transition means is substantially coaxial cable-like in configuration and the parallel plate end of the transition means has a parallel plate-like configuration. Included in the transition means is a first conductor configured to provide a smooth transition between a coaxial cable outer conductor and a first plate of the parallel plate end of the transition means, and a second conductor configured to provide a smooth transition between a coaxial cable inner conductor and a second plate of the parallel plate end of the transition means.

Since the coaxial cable is ordinarily small in diameter, the transition means also preferably includes diverging means at the coaxial cable end for increasing the size of at least one of the conductors, while maintaining the characteristic impedance of the transition means throughout the dynamic frequency range.

The transition means may be either air filled or dielectrically filled, and is also adapted, although not at constant characteristic impedance, for providing transition between coaxial and parallel plate transmission lines having different impedances, as may sometimes be necessary.

Also in accordance with one embodiment of the present invention, and constituting also a separately useful component, the applicator includes a radiating chamber having parallel, spaced apart top and bottom conductive plates, with a first conductive end plate interconnecting first ends of the top and bottom plates. Further, a second conductive plate, having a first end connected to a second end of the top plate, has a height equal to at least about half the spacing between the top and bottom plates. Radiating ends of first and second launching means plates, which converge in width and separation to maintain constant characteristic impedance, are connected, respectively, to the second ends of the second end plate and the bottom plate.

The length of the resonator chamber is equal to about one half the wavelength of a selected electromagnetic radiation frequency within the dynamic frequency range so that standing electromagnetic waves are created within a resonator cavity.

For an alternative type of applicator in accordance with the invention, the launching means thereof is dielectrically filled and includes first and second electronically conductive, opposing walls each having a source end connected to included transition element conductors. Width of the walls and separation therebetween is increased towards the emitting ends thereof to maintain a substantially constant characteristic impedance at substantially all transverse sections, over a electromagnetic dynamic frequency range of at least about 5 to 1. The applicator includes a field coupling means, which in turn includes first and second conductive flaps connected to the emitting ends of the launching means walls for improved radiation coupling with tissue and tissue simulating matter being irradiated.

For further improved radiation coupling and heating, a plurality of the above mentioned alternative type may be arranged in flap overlapping relationship around tissue or tissue simulating matter, for example a human limb, to thereby form a radiating cavity loaded by the tissue to be irradiated. In this manner, improved electromagnetic radiation deep heating is provided in central regions of the tissue mass.

A better understanding of the present invention may be had from a consideration of the following detailed description, taken in conjunction with the accompanying drawings in which:

FIG. 4 is a perspective drawing of an alternative, dielectrically filled coaxial to parallel plate transition means;

FIG. 5 is a sequence of transverse sectional views, taken along lines 5(a)—5(a) through 5(f)—5(f) of FIG. 4, showing enlargement of coaxial end portions of the transition means and showing the coaxial to parallel plate transition;

FIG. 6 is a partially cutaway perspective drawing of an whole body electromagnetic radiation applicator according to the present invention, showing incorporation of the transition means of FIG. 2;

FIG. 7 is a partially cutaway, side elevational view of the applicator of FIG. 6, showing features thereof;

FIG. 9 is a sequence of transverse sectional views, taken along lines 9(a)—9(a) through 9(c)—9(c) of FIG. 8, showing width and spacing divergence of the launching means portion;

FIG. 10 is a perspective drawing of an alternate, dielectrically filled, partial body applicator incorporating the dielectrically filled transition means of FIG. 4;

FIG. 11 is an elevational cross sectional view of the dielectrically filled applicator of FIG. 10, showing the applicator in operational relationship with portions of a body or test specimen;

FIG. 12 is a transverse sectional view along line 12—12 of FIG. 11, showing features of the dielectrically filled applicator;

Figure 1:
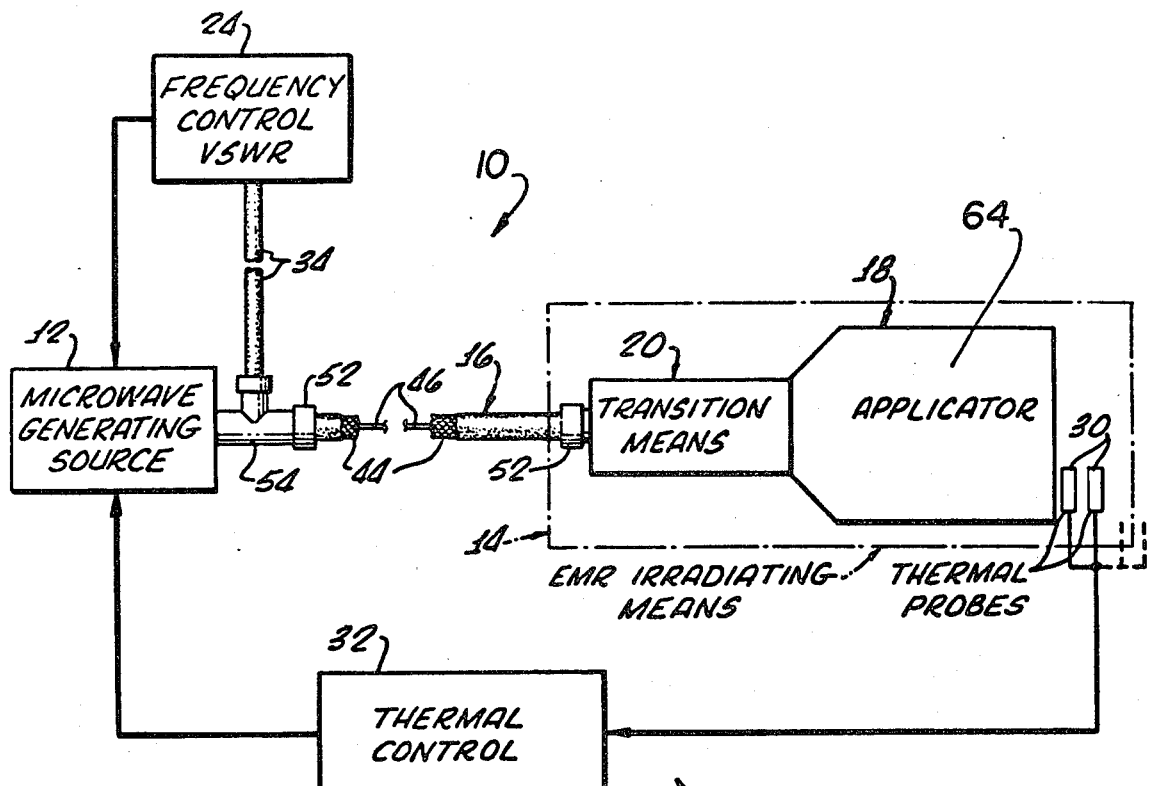
FIG. 1 is a block diagram of a broadband electromagnetic radiation apparatus, according to the present invention, for irradiating living tissue or tissue simulating material.

As seen in FIG. 1, a broadband electromagnetic radiation (EMR) system or apparatus 10 for irradiation of living tissue or tissue simulating material comprises generally an EMR or microwave generator or source 12 to which is electrically connected, by a transmission means or line 16, EMR irradiating means 14.

Included in the irradiating means 14 are an applicator or applicator means 18 and broadband transition means 20 for providing substantially reflectionless EMR transmission between the transmission line 16 and the applicator 18, as more particularly described below.

Additionally comprising the EMR apparatus 10 are thermal monitoring and control means 22 and frequency monitoring and control means 24.

The thermal monitoring and control means includes one or more temperature probes 30, for example, nonperturbating thermocouples, for monitoring tissue or test specimen temperatures during EMR irradiation. Thermal control means 32 to which the temperature probes 30 are electrically connected are preferably of a programmable type by means of which temperature-time irradiation profiles can be preselected, the control being connected to the generator 12 to control operation thereof to achieve the preselected profile.

EMR frequency output of the generator 12 may be controlled by the frequency monitoring and control means 24 which includes, for example, a voltage standing wave ratio (VSWR) meter connected by a line 34 into the transmission line 16 adjacent to the generator 12 for measuring EMR energy reflected theretowards. The frequency control means is particularly useful in uses requiring reflected EMR energy to be at a minimum or below a preselected minimum when the reflected energy is a function of applied energy, for example, in operation of whole body type applicators, as described below.

Both the thermal and frequency and monitoring control means 22 and 24 are considered to be of conventional configuration and form no part of the present invention.

Because, as described below, impedances are closely matched throughout, the apparatus 10 has good efficiency throughout a broad dynamic frequency range, or bandwidth ratio of at least 5 to 1, and preferably 10 to 1. Accordingly, most of the electromagnetic energy provided by the generator 12 is applied by the applicator 18 to tissue or tissue simulating test specimens. In this regard, as used herein the term tissue is understood to include all the various constituents of the body such as skin, fat, muscle, bones and organs.

Since the generator 12 is not required to generate very much more EMR energy than is required to be applied by the applicator 18, relatively low cost generators can be used. As an illustration, the generator may be a model 15152 radio frequency power generator available from the Microwave Components Laboratory Company. Such type of generator 12 has a typical power output of 100 watts and operates over a frequency range of about 10 MHz to 2500 MHz as has been found useful in many applications. However, for applications requiring higher power levels or different frequency ranges, other, comparable generators may alternatively be used, higher power generators being available, for example, from the above mentioned company.

As noted, the generator 12 should have a dynamic frequency range of at least 5 to 1 and preferably 10 to 1 to enable broadband system operation, as is desirable to investigate such EMR hyperthermia effects as heating at different frequencies, EMR penetration in different tissue compositions, as well as such other medically related effects as heating bodies or portions thereof after hypothermia conditions(such as low temperature operations). Broad band operation also enables investigation of low level, nonthermal EMR effects at all desired hyperthermia frequencies.

Relatively high efficiency of the EMR apparatus 10 is achieved in large part, over the broad dynamic frequency range of operation, by matching impedances throughout as closely as possible. Towards this end, characteristic impedences, $Z_o$, of transmission line portions, including the line 16, the transition means 20 and the applicator 18 are selected to match the characteristic impedance of the tissue or tissue simulating material to be irradiated.

As used herein, and as generally defined, characteristic impedence, $Z_o$, is that impedance which a transmission line infinite in length presents at an input end thereof. When a transmission line which is finite in length is terminated in an impedance equal to the line characteristic impedance, the line appears, insofar as EMR applied energy if concerned, as infinite in length. The importance of a transmission line appearing infinite in length to applied energy is that no EMR reflections occur.

Since the apparatus 10 is configured for irradiating, particularly in a medical research environment, living tissue, such as animal or human tissue, or simultaneous thereof, the characteristic impedance of human tissue is selected as the characteristic impedance to be matched throughout.

Although different portions or layers of human tissue are considered to have different impedances, depending largely upon water content, average tissue impedance, at least over an approximate frequency range of 50 to 2000 MHz, has been determined to be approximately 50 ohms. This value of tissue impedance conveniently permits use of conventional 50 ohm coaxial cable for the transmission line 16 and also to use generally standar EMR generators having 50 ohm output impedances over the entire selected dynamic frequency range.

Accordingly, as described below, at least parallel plate input or launching portion of the applicator 18 are configured to have 50 ohm characteristic impedences over the entire selected frequency range. Also as described below, the transition means 20 is configured to have a characteristic impedance of 50 ohms throughout the dynamic frequency range.

Figure 2:
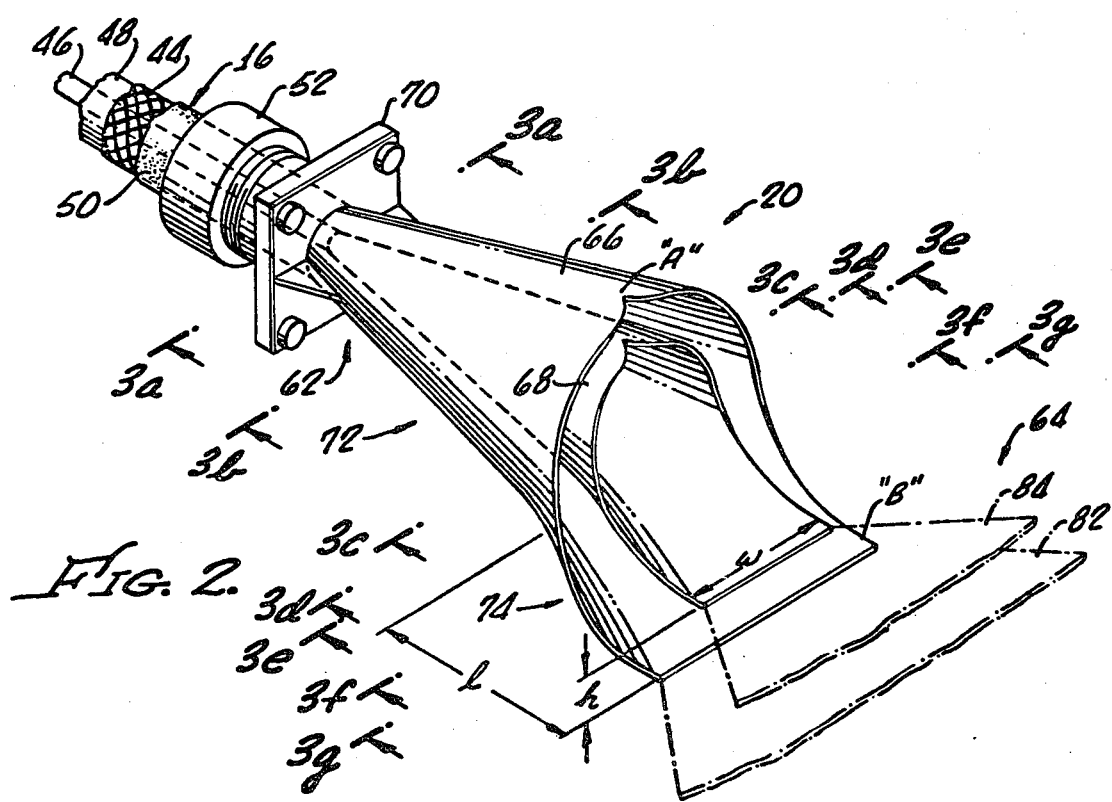
FIG. 2 is a perspective drawing of coaxial to parallel plate transition means portions of the apparatus of FIG. 1.
Figure 8:
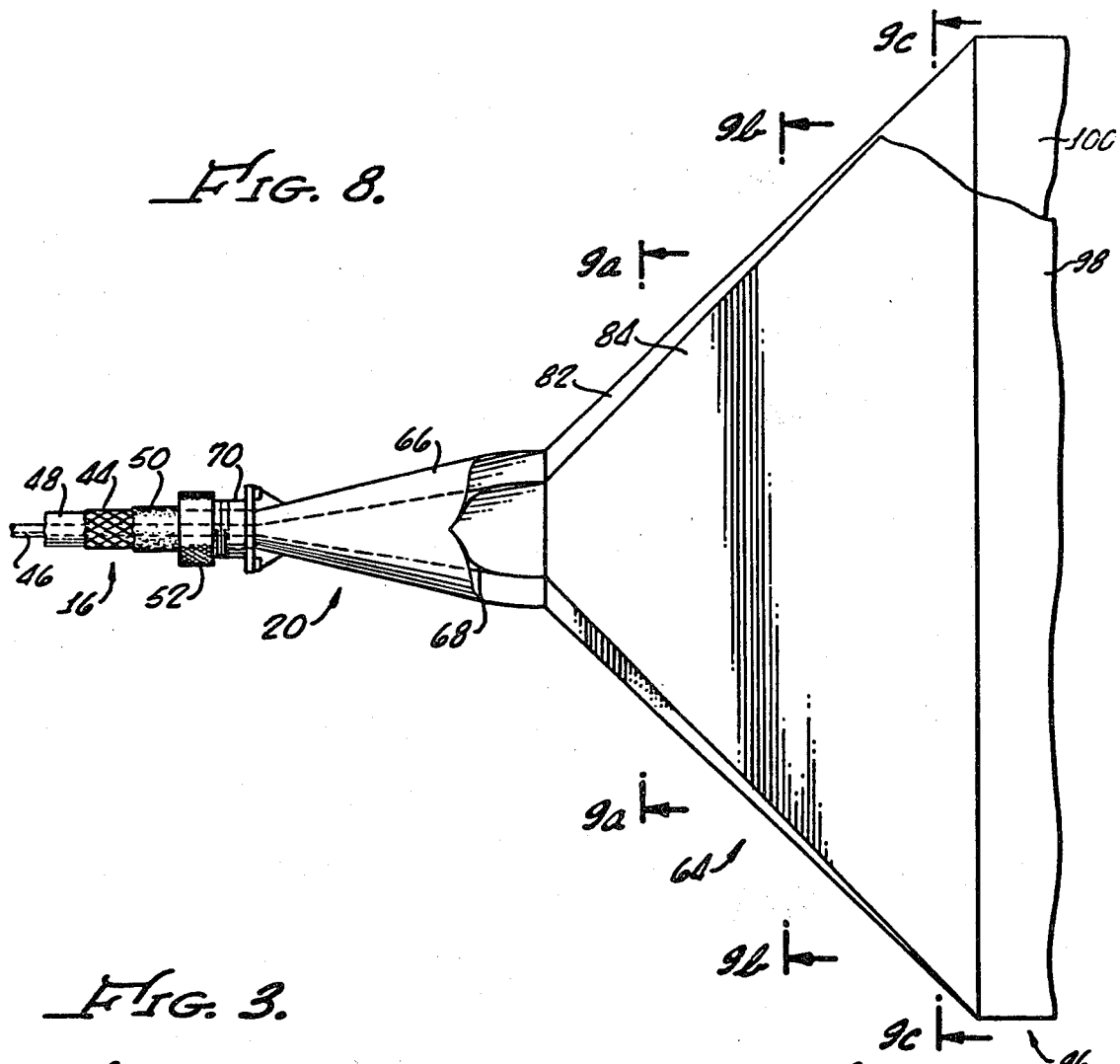
FIG. 8 is a partial, top plan view of the applicator of FIG. 6, showing transition means and launching means portions thereof.

Assuming the transmission line 46 is coaxial in configuration, as seen in FIG. 2, such line comprises cylindrical inner and outer conductors 44 and 46, respectively, which are separated by a dielectric layer 48. An insulating layer 50 surrounds the outer conductor 46. Ends of the coaxial cable are terminated in conventional fittings or connectors 52. The connector 52 at an input end of the coaxial cable is shown, in FIG. 1, connected to a conventional coaxial tee fitting 54 at the generator 12. The line 34 associated with the frequency monitoring and control means 24 is also shown connected to the same fitting 54.

Further assuming, for the type of applicators described herein, that input portions or launching means 64 included in the applicators are parallel plate in configuration, coaxial to parallel plate transition is required. However, direct stepping from coaxial to parallel plate transmission line configuration, for example, by using conventional coaxial bulkhead fittings, may cause an excessively abrupt step, even when the lines themselves have the same characteristic impedances. This step results from abrupt geometric changes. As a result, such abrupt coaxial to parallel plate connections can cause local higher order modes which generally result in excessive stray radiation and lower efficiency. These transmitters typically have very close and critical spacing between the parallel plates, such spacing also limiting the maximum power capability.

Accordingly, although conventional bulkhead fitting transitions having the stated deficiencies could be used, the transition means 20 is specifically configured to provide $Z_o$ matching interconnection between the line 16 and parallel plate launching means 64, which is substantially EMR reflectionless over the entire selected dynamic frequency range.

Figure 3:
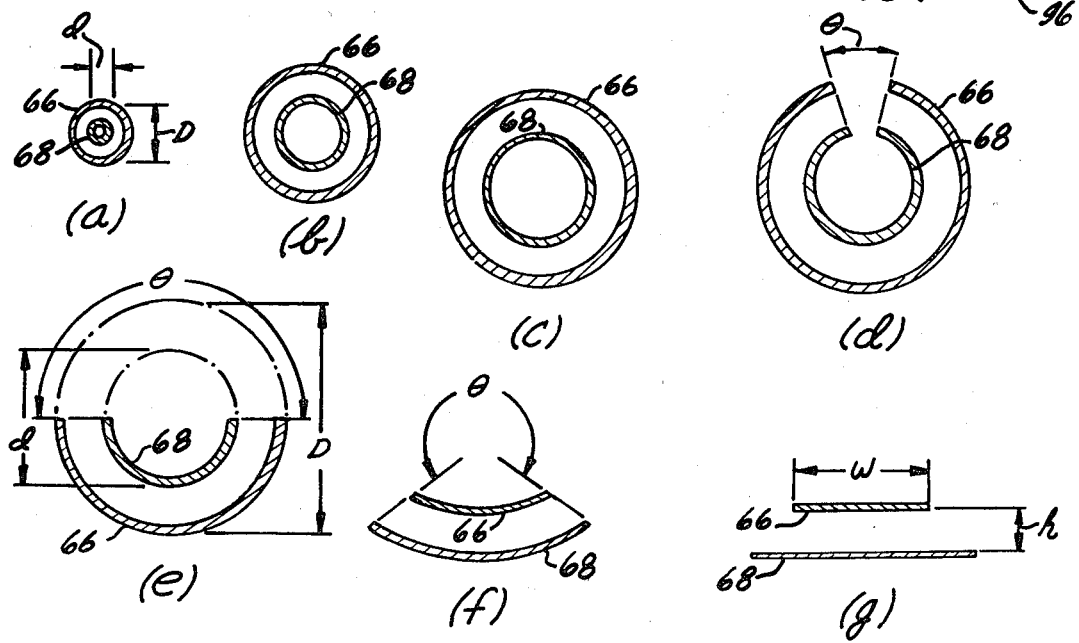
FIG. 3 is a sequence of transverse sectional views, taken along line 3(a)—3(a) through 3(g)—3(g) of FIG. 2, showing enlargement of coaxial end portions of the transition means and showing the coaxial to parallel plate transition.

In general, such $Z_o$ matching is achieved by configuring a smoothly continuous and comparatively gradual mechanical and electrical transition of outer and inner conductors 66 and 68, respectively, of the transition means 20 from a coaxial input end configuration to a parallel plate output (or EMR launching) end configuration, as shown in FIGS. 2 and 3. Such transition is specifically configured not only to provide a comparatively gradual transition but also to maintain a constant $Z_o$ of 50 ohms (for the example described) at all transverse sections thereof.

It should be understood that for purposes of description herein, and as is generally accepted in the industry, the term "parallel plate" as applied to two conductor transmission line does not require that planes of the conductors actually be parallel throughout. All that is required for conventional parallel plate transmission line analysis to apply is that the two conductors, as seen in all transverse cross sections, appear parallel. As long as this condition is met, actual planes of the conductors may diverge, as described below, or may converge.

Configuration of the transition means 20 to achieve constant $Z_o$ coaxial to parallel plate transition is accordingly governed by coaxial and parallel plate transmission line equations and/or design curves. For a two conductor coaxial cable, characteristic impedance, $Z_o$, is expressed by the well known formula:

$$Z_o = \frac{138}{\sqrt{e}} \log_{10}(D/d) \qquad (1)$$

In which e is the dielectric constant of the dielectric between the conductors, D is the inner diameter of the outer conductor and d is the outer diameter of the inner conductor.

Parallel plate transmission line design is governed by plots of $Z_o$ versus conductor width (w) to spacing (h) ratio, as found, for example, in the MICROWAVE ENGINEERS HANDBOOK, Vol. 1, by Saad, published by ARTECH HOUSE, INC. Generally for a given dielectric between the conductors, as the ratio w/h increases, $Z_o$ decreases. Also, at a constant w/h ratio, $Z_o$ increases with decreasing dielectric constant.

For the foregoing equation (1), and referring to such plots as mentioned, it is seen that for air filled transmission lines (e=1), to achieve $Z_o$ equals 50 ohms, for coaxial cables the ratio D/d must equal 2.31 and for parallel plates the ratio w/h must equal about 5.

An additional factor considered, and described for illustrative purposes, is that at least for low power levels, diameters of the coaxial conductors are relatively small, for example D may be only about 0.37 inches. As a result, smooth coaxial to parallel plate may be physically difficult to achieve. In addition, to assist in visual inspection and evaluation of the transition means 20 after forming thereof, the transition means is preferably configured such that spacing between the conductors 66 and 68 at both the coaxial and parallel plate ends is basically identical. This enables spacing between the conductors 66 and 68 to be kept constant during the transition.

A further consideration is that for transition between a dielectrically filled coaxial cable (the line 16) and air filled parallel plate launching means 64, compensation must be made for change in dielectric constant.

This compensation is most easily made at the input end of the transition means 20, assuming the transition means is to be air filled. From equation (1) is seen that for $Z_o$ to remain constant when e changes, the ratio D/d must be changed. Assuming e of the line 16 is equal to 2.1 and that the initial D of the conductors 66 is at the 0.37 inches of the coaxial conductor 44, d of the transition means inner conductor 68 is stepped from the 0.11 inches of the coaxial inner conductor 46 to 0.16 inches, thus, D/d equals 2.31 as is required for $Z_o$ equal 50 ohms. Such stepping is most conveniently made at a transition means input connector 70.

To increase size of the conductors 66 and 68 and to achieve the desired spacing, h, at the parallel plate end, the conductors are flared outwardly in a longitudinal, diverging region 72. Throughout the length of such diverging region 72, the ratio D/d for the conductors 66 and 68 is maintained at 2.31 to keep $Z_o$ constant at 50 ohms. Flairing of the conductors 66 and 68 is such that, at Point A, FIG. 2, D equals one inch, d equals about 0.43 inches and spacing between the conductors is 0.285 inches, which is equal to a selected initial parallel plate separation, h.

In a longitudinal transition region 74, which extends from Point "A" to a Point "B", the conductors 66 and 68 are axially split along upper regions and are gradually opened out and flattened into parallel plate configuration (FIGS. 3(d)-3(g)). At Point "B", the outer connector 68 is continued, or connected to, a conductive lower plate 82 which forms an extension thereof, and the inner conductor 68 is similarly continued into, or connected to, a corresponding, opposing conductive upper plate 84 which forms an extension thereof. As described below, the plates 82 and 84 typically comprise the launching means 64 of the associated applicator 18.

Between the Points "A" and "B", transition of the conductors 66 and 68 is thus made between an initial coaxial configuration in which D=1 inch and d=0.43 inches to a parallel plate configuration in which width, w, of the inner conductor 68 and the upper plate 84 at their junction is equal to 0.68 inches (one half the circumference of the inner conductor at Point "A") and initial spacing, h, between the plates 84 and 82 is equal to 0.14 inches (w/h=5). Width of the outer conductor 66 is narrowed to about 2¼ inches for convenience, width of the bottom plate 82 being non-critical so long as such width is not reduced below width w.

As long as length, 1, (FIG. 2) of the transition region 74 is not less than D at Point "A" of the transition region 74, high transition efficiency, as measured by the amount of EMR reflection, is attained by making the described smooth, relatively gradual transition of the conductors 66 and 68 from coaxial to parallel plate cross section.

Since, however, the transition outer diameter D, must always be less than about half of a wave length to prevent causing undesirable frequency moding, at higher frequencies, for example above 10 GHz, an additional factor may have to be considered to minimize or eliminate EMR reflection in the transition means 20. This factor involves the manner or rate at which $Z_o$ changes as the conductors 66 and 68 are opened up.

As seen, for example, in the REFERENCE DATA FOR RADIO ENGINEERS, 5th Edition, published by Howard Sams and Co., the manner in which $Z_o$ changes for a split line conductor is given by the expression:

$$\Delta Z_o = 0.03 \, \theta^2 \qquad (2)$$

in which $\Delta Z_o$ is the change in $Z_o$, and $\theta$ is the conductor opening angle (as seen in FIGS. 3(d)-(f)) expressed in radians.

As an example of the manner in which equations (1) and (2) are applied together to obtain a constant $Z_o$ during configuring the transition means $Z_o$ for high frequencies, assume that $\theta = \pi$ radians (180°), as seen in FIG. 3(e). From equation (2), for $\theta = \pi$, $\Delta Z_o$ is calculated to be about 0.30 or 30%. That is, by opening the conductors 66 and 68 up through 180 degrees, $Z_o$ as otherwise calculated by equation (1) increases by 30%. If the initial D/d of 2.31 for $Z_o$ were maintained (both D and d obviously increase as the conductors 66 and 68 are opened up) $Z_o$ at $\theta$ equals 180 degrees would be about 65 ohms.

To compensate for this $Z_o$ increase with $\theta$, the ratio D/d must be decreased by an amount reducing $Z_o$ calculated by equation (1) by 30 percent, or to about 35 ohms. Thus D/d at $\theta = 180°$ must be about 1.8 rather than 2.31. In the example, given, this would change w to 0.87 inches from 0.68 inches.

Simular changes in configuration of the conductors 66 and 68 to achieve the appropriate D/d ratio are made at all other angles of $\theta$ up to about 270 degrees, (FIG. 3(f)), at which angle the conductors are close to parallel plate configuration.

The described application of equation (2) may also be used to determine transition means configuration at lower frequencies if desired.

An additional example of providing constant $Z_o$ transition between coaxial and parallel plate EMR transmission lines is seen in FIGS. 4 and 5 for a dielectrically filled type of transition means 20a. This alternative transition means 20a is particularly useful in conjunction with dielectrically filled applicator means, described below.

Because the dielectric constant of the coaxial line dielectric layer 48 is relatively low (2.1), dielectric material for the transition means 20a having a constant in the range of about 7-12 is desirable, a value of 7 being assumed for purposes of description herein.

From equation (1), it is apparent that for $Z_o$ to remain constant when the dielectric constant is changed, the ratio D/d must be changed. Thus, as shown in FIGS. 4 and 5, when making an abrupt transition from the line 16 having a dielectric constant of 2.1 to the transition means 20a which is to be filled with a dielectric having a constant of 7, while maintaining $Z_o$ at 50 ohms, either D or d must be changed. For illustrative purposes, an outer coaxial conductor 66a is accordingly stepped, in a region 72a, to approximately 0.9 inches while the diameter d, of an inner conductor 68a, is kept the same as that of the coaxial line inner conductor 46 at 0.11 inches, which provides about 0.4 inches conductor spacing.

It should be noted that changing both D and d at the point where e changes generally yields unsatisfactory results.

Although the coaxial to parallel plate transition is otherwise generally made in the manner described above for the air filled transition means 20, the smaller diameter inner conductor 68a requires some variation. Since the inner conductor 68a is too small to be readily opened up and flattened out, a flat plate 86 of diverging width is fixed to the end of such conductor at the start of a coaxial to parallel plate transition region 74a. As the split outer conductor 66a is opened up, width of the plate 90 is increased to maintain an approximately uniform spacing between all regions at the plate and the outer conductor.

Were the plate 86 not added to the inner conductor 68a, as the outer conductor 66a opened out and flattened, outer conductor edge regions 88 (FIG. 5(d)) would be farther from the inner conductor 68a than central regions 90, causing an uneven electromagnetic field and a change in $Z_o$.

For the exemplary configuration, distance between side edges 92 of the plate 86 and adjacent outer conductor regions 88 is maintained at 0.4 inches. For an opening angle, $\theta$ of, for example, 180°, width of the plate 86 is 0.13 inches. As $\theta$ is increased to about 270°, width of the plate 86 is increased to 0.3 inches. When the transition to parallel plate configuration is completed, plate width, w is 0.51 inches and plate separation, h is 0.4 inches, resulting in a w/h ratio of 1.28, as is required for a $Z_o$ of 50 ohms at E=7. Width of the flattened outer conductor at Point B, when transition to parallel plate, configuration is complete, may be reduced to about 1.4 inches for convenience.

Some improvement in $Z_o$ matching during the coaxial to parallel plate transition may be provided by curving the plate 86 so that the transition is more nearly like that shown in FIGS. 2 and 3 for the transition means 20 with the result that equations (1) and (2) can be directly applied.

Parallel plate ends of the plate 86 and the outer conductor 66a are shown (FIG. 4) connected to diverging plates 84a and 82a, respectively, which may form EMR launching or input portions 64a of an associated applicator 18a as described below. When construction of the transition means 20a is completed, internal regions between the conductors are dielectrically filled, as shown in phantom lines in FIG. 5.

In a similar manner, virtually any other type of constant impedance, coaxial to parallel plate transition can be constructed, including those types associated with coaxial and parallel plate lines filled with different dielectric constant material. Also, in an analogous manner, primary mode transition, although not at constant $Z_o$, may be effected between coaxial and parallel plate transmission lines having different characteristic impedances, as may in some instances be necessary or desirable.

Furthermore, although the coaxial line 16 has been described as connected to input ends of the transition means 20 and 20a, and the parallel plate conductors 82, 82a and 84, 84a as connected to output ends thereof, designation of input and output ends is arbitrary. That is, direction of EMR wave travel through the transition means 20 and 20a is immaterial, the transition means being bidirectional.

APPLICATOR MEANS

The air filled transition means 20 is particularly adapted for use with air filled applicators. Thus, in FIG. 6-9, the transition means 20 is shown connected to the diverging input region of EMR launching means 64 associated with the applicator 18, which is of an air filled, whole body, parallel plate type. Additionally comprising the applicator 18 is a terminating resonant chamber or resonator 96 configured for receiving and irradiating at least major portions of a body or body simulating test specimen. Together the transition means 20 and the applicator 18 comprises the EMR irradiating means 14 of FIG. 1.

Forming the resonator 96 are parallel, opposing first and second conductive plates 98 and 100, respectively, which are shown as forming upper and lower resonator surfaces. Electrically interconnecting, to short together, remote ends of the plates 98 and 100 is a conductive first end wall 102. Although shown as completely closing an end of the resonator 96, the end wall 102 may be formed having one or more openings through which portions of a body not intended to be irradiated may project.

A conductive, second partial end wall 104 is connected along an upper edge thereof to an input end of the first upper plate 98 to depend therefrom. Preferably, as below explained, the second end wall 104 extends at least about half way downwardly towards the second, lower plate 100 so that the input end of the resonator 96 is at least half closed. A resonant cavity 106 is thereby defined in the resonator 96 by the plates 98 and 100 and the end walls 102 and 104.

An output or launching end of the plate 84, which forms an upper conductive surface of the launching means 64, is connected to a lower edge 108 of the second end wall 104. A corresponding end of the plate 82, which forms a lower conductive surface of the launching means 64, is connected to, or formed continuously with, the resonator second, lower plate 98. Width, w. of the upper plate 84 and separation, h, between the plates 82 and 84 are increased in a manner maintaining the ratio w/h equal to 5, as is necessary to maintain a constant $Z_o$ of 50 ohms at all transverse sections of the launching means 94.

An EMR emitting or launching opening 110 is defined between the second end wall edge 108 and the below adjacent intersection of the plates 82 and 98. (FIGS. 6 and 7). When length of the resonator 98 is equal to half the wave length of radiation emitted through the opening 110, standing EMR waves will result in the cavity 106, the resonator thus acting as a half wave length termination to the launching means 84.

It is to be appreciated that when a body or test specimen is received in the cavity 106, dielectric properties of the body or specimen cause the effective or EMR apparent length of the resonator 96 to increase slightly, the extent of such increase depending upon the extent to which the body or specimen fills the cavity 106, that is, upon the "fill factor". The greater the fill factor, the greater the effective increase in resonator length will be. As a result, the applied frequency causing resonance varies with fill factor, and may be controlled by the frequency means 24.

At the resonant frequency, when the fill factor is high, EMR energy is rapidly absorbed from the standing waves, within several reflections, by a body or test specimen enclosed in the resonator 96. However, if the fill factor is so high that energy is rapidly absorbed in less than several wave reflectors, non-uniform EMR heating of the body or specimen tends to occur. If, on the other hand, the fill factor is low, an excessive number of wave reflections between the resonator end walls 102 and 104 occur before absorption, thereby permitting more radiation leakage from the resonator 96.

To reduce radiation leakage from the sides of the resonator 96, particularly when the fill factor is low or at frequencies other than the resonant frequency, conductive first and second partial side walls 118 and 120, respectively, are connected in depending relationship to opposite sides of the upper plate 98, thereby partially closing sides of the resonator. Radiation leakage from the sides of the launching means 64 is similarly minimized by conductive first and second partial side walls 122 and 124 which depend from side edges of the upper plate 84. Preferably the side walls 118, 120 and 122, 124 cover about half of their respective side openings.

The launching means 64 is configured to have a constant $Z_o$ of 50 ohms along the length thereof, over the entire dynamic frequency range, as is necessary for efficient broadband operation; however, an impedance mismatch occurs at the launching means—resonator interface because of dimensional changes introduced by the second end wall 104 which partially defines the cavity 106.

If a w/h ratio of about two is assumed, as has been found both practical and useful, for the resonator 96, when no body or specimen is received in the cavity 106, from the above mentioned w/h curves $Z_o$ is 90, for e equals one. When the cavity contains a body or test specimen of human shape having an assumed dielectric constant of about 49, resonator $Z_o$ varies between approximately 35 to 90 ohms, because of the non symmetrical body shape.

An effect of the resulting $Z_o$ step is that whenever the launching means 64 radiates EMR energy into the cavity 106 through the opening 110, some radiated energy is reflected back down the launching means. Additional emitted energy is reflected down the launching means 94 by the end wall 102. Since, waves reflected from the end wall 102 are inverted, while those reflected by the $Z_o$ step at the launching means—resonator interface are not, reflected wave cancellation tends to occur in the launching means. Thus, the $Z_o$ step, caused in part by the launching opening 110 being smaller than the input end of the resonator 96, provides a reflection cancelling effect.

Although the amount of the $Z_o$ step can be varied by varying w/h of the resonator 96, to minimize total wave reflection down the launching means 64 at a particular frequency narrow range of frequencies, total reflection will be greater at other frequencies. Thus, efficiency, as measured by the amount reflected energy, varies with applied frequency.

Nevertheless, broadband capabilities of the launching means 64 are still very advantageous for investigating such variables as orientation of loading the cavity 106, fill factors and resonator configuration.

By suitably dimensioning the resonator 96, a body loaded resonator $Z_o$ of about 50 ohms could be obtained. However, some energy reflection would still occur, since stepping at the launching means—resonator interface of both resonator w and h would be necessary because of dielectric change when the resonator 96 is loaded, assuming the partially closed end wall is used to cause standing waves in the resonator.

Typically the amount of the $Z_o$ step can be varied, by varying w/h of the resonator 96, to minimize the uncancelled EMR waves and total reflected power.

An alternative, dielectrically filled, partial body EMR applicator 18a, which incorporates, at an input end, the dielectrically filled transition means 20a is illustrated in FIGS. 10–12. Included in the dielectrically filled applicator 18a, which is in many respects similar to the above described air filled applicator 18, are input or launching means 64a, corresponding to the air filled launching means 64. Such launching means 64a has a conductive upper surface defined by the plate 84a which is connected to the transition means center conductor plate 86. A conductive lower surface of the launching means 64a is defined by the plate 82a which is connected to the transition means outer conductor 66a.

Both width, w, of the plate 84a of the launching means 64a and separation, h, of the plates 84a and 82a diverge in a direction away from the transition means 20a in a manner maintaining the ratio w/h constant. Assuming the launching means 64a is filled or loaded with a dielectric 130 having a dielectric constant of 7, as was above described for the transition means 20a, to keep $Z_o$ constant at 50 ohms at all transverse sections of the launching means, a w/h ratio of 1.28 is maintained throughout.

Because the launching means 64a is dielectrically filled, under normal operating condictions little side electromagnetic radiation into the air from between the plates 82a and 84a occurs. However, such leakage is minimized by connecting conductive, first and second partial upper side plates 122a and 124a, respectively, along opposite side edges of the upper plate 84a. Similar conductive first and second partial lower side plates 138 and 140, respectively, are connected along opposite side edges of the lower plate 82a. In combination, the upper and lower side plates 122a, 124a, 138 and 140 cover about half of the side areas between the plates 82a and 84a.

A flat, exposed irradiating or EMR launching surface 142 of the dielectric 130 is formed at an applying end of the launching means 64a. For illustrative purposes, the launching surface 142 is shown in FIG. 11 in contact with an exposed surface 144 of a body or test specimen portion 146 to be irradiated by the applicator means 18a. Accordingly, the engaged body or specimen portion 146 functions as a termination of the applicator 13a, an average termination impedance of approximately 50 ohms being thereby provided, as has been used in configurating portions of the system to have characteristic impedances of 50 ohms.

Ordinarily the entire launching surface 142 cannot be placed in direct contact with the body or specimen surface 144, because of relative differences in size and shape. Consequently, small air gaps 148 typically occur along edges of the launching surface 142 and tend to cause non-uniform coupling of the applied EMR field to the body or specimen portion 146 and radiation leakage to the surroundings.

To improve coupling of the field from the applicator 18a into the body or speciman portion 146 and substantially reduce leakage effects of the air gaps 148, first and second conductive flaps 150 and 152 are electrically connected, respectively, to output or launching ends of the plates 82a and 84a, to provide extensions thereof. Preferably, the flaps 150 and 152 are pivotally connected to the plates 82a and 84a and are flexible or bendable to enable at least partially wrapping around the body or specimen portion 146 and conforming to the surface 144 thereof. When the flaps 150 and 152 are "loaded" with the body or specimen portion 146 which functions as a dielectric, characteristic flap impedance of about 50 ohms is maintained. The electric field, represented by field lines 158 in the region of the flaps 150 and 152 for applied EMR waves traveling in the direction of Arrow "C" into the portion 146, (FIG. 11) indicate the manner in which the flaps, which function as strip line transmission lines, couple the field into the specimen.

Figure 13:
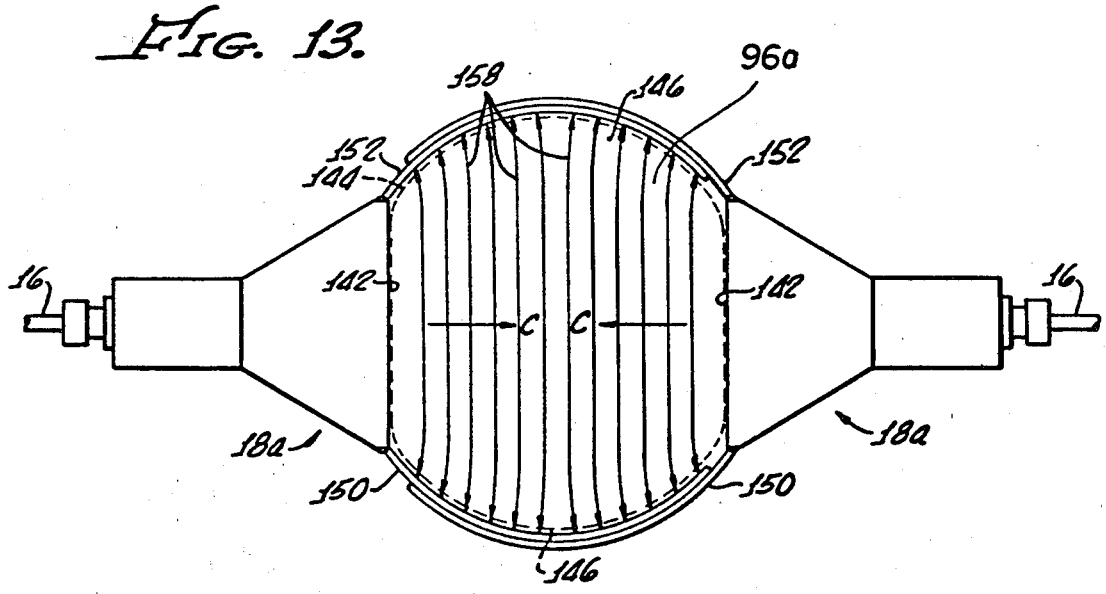
FIG. 13 is a drawing similar to FIG. 11, showing a pair of dielectrically filled applicator positioned in partial overlapping relationship around portions of a body or test specimen.

This field coupling effect of the flaps 150 and 152 into the body or specimen portion 146 is very important, and indicates an advantageous manner in which two (or more) of the applicators 18a can be arranged in opposing relationship to form a radiating chamber 96a (FIG. 13). When the respective flaps 150 and 152 are overlapped in the manner illustrated, a resonant cavity 106a, which corresponds generally to the cavity 106 of the whole body resonator 96, is formed. As was described for an enclosed body in the resonator 96, the body or specimen portion 146 enclosed in the resonator cavity 106a, dielectrically loads the cavity.

The illustrated dual applicator arrangement results in central intensification of EMR power when both the applicators are emitting radiation having the same frequency, amplitude and phase. Accordingly, greater power is delivered in the central, flap overlapped region of the specimen with resulting deeper heating of the body or specimen portion 146 than normally occurs with use of only a single applicator.

Electrical shorting between opposing pairs of plates 82a and 84a and flaps 150 and 152 forming the applicator parallel plate or strip line transmission line is prevented by an insulating layer 154 applied over all otherwise exposed exterior surfaces of the plates and flaps.

Although dimensions of the launching means 64a may be varied according to particular use intended, some limitations exist as to the separation, h, between the plates 82a and 84a. When such separation, h, approaches ¼ to ½ of the wave length of the EMR frequencies being applied, side radiation leakage occurs and efficiency decreases. Consequently, as h is increased, the upper limit of applied frequency must normally be reduced. Such limitation similarly applies to the air filled launching means 64.

Figure 14:
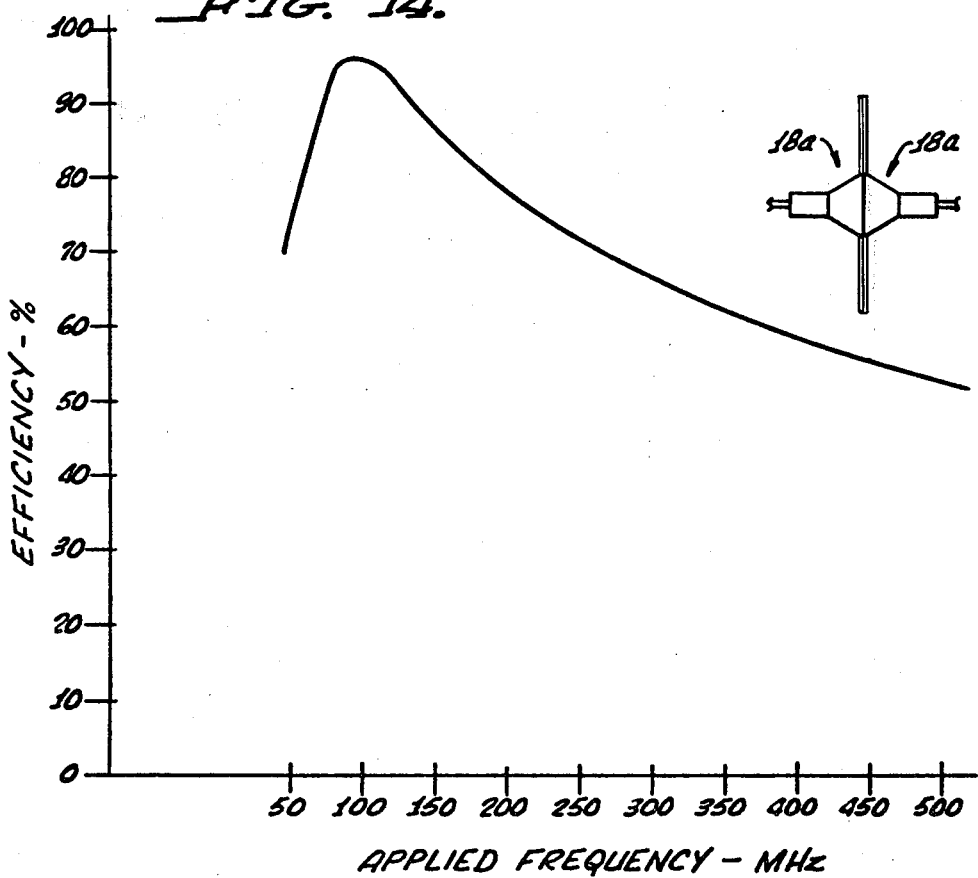
FIG. 14 is a plot of efficiency Vs. frequency for dielectrically filled applicator of the type shown in FIG. 10.

For a particular size of the applicator 18a in which the launching surface 142 is 5.30 inches wide (equal to w) and 4.12 inches high (equal to h) and with flaps 150 and 152 at least about 5 inches long, efficiency at various applied EMR frequencies has been measured and plotted (FIG. 14). To enable efficiency measurements, a pair of similar applicators 18a were arranged in face-to-face relationship, with corresponding launching surfaces 142 and flaps 150 and 152 in abutment. One of the applicators 18a was used to emit radiation over a frequency range from about 50 MHz to 500 MHz while the other was used as a receiving antenna.

Applicator efficiency, for the plot shown in FIG. 14, is defined by the ratio of EMR power received by the receiving one of the applicators 18a to power applied to the emitting one of the applicators. As indicated efficiency has a maximum of over 90 percent in the 100–150 MHz range. Above 150 MHz, efficiency decreased to about 55 percent at 500 MHz due to plate separation, h, approaching a half wave length condition. Below about 100 MHz, efficiency also decreased as the amount of wave reflections increased, thereby affecting coupling between the two applicators.

Efficiencies, when the applicator 13a is actually used in the manner intended, are expected to be higher than those shown, the efficiency curve shown being considered to represent a minimum efficiency curve. Nevertheless, the relatively high efficiencies obtained over the 10 to 1 dynamic frequency range demonstrate the broadband capabilities of the applicator 18a.

Radiation leakage measurements made at power levels of about 50 watts and at frequencies in the 260–275 MHz range indicated that radiation leakage levels at distances of more than about four inches from the applicator 18a are less than about 10 MW per square centimeter.

Efficiencies and radiation leakage of the air filled launching means 64 are expected to be similar to those of the dielectrically filled applicator 18a.

Although measured levels of radiation leakage under the specific conditions noted are below levels currently considered hazardous, under other use conditions leakage may be higher and leakage monitoring is desirable. And since the Federal Communications Commission has allocated only several discrete radio frequencies to diathermy and medical use, shielding of the system 10 or portions to prevent interference with communication may be required even if shielding to prevent hazardous conditions to users is not.

Although the applicators 18 and 18a are considered very efficient considering their broadband operational capabilities, improvements in applicators are continually sought so that more controlled and more uniform EMR fields can utimately be applied to human patients for hyperthermia treatments. For this purpose, as well as such before mentioned purposes of investigating EMR heating at different body depths and at different frequencies and investigating occurance of irradiation hot spots in tissue, broadband EMR apparatus is extremely important.

Although there has been described above specific arrangements of efficient, broadband electromagnetic radiation apparatus and related coaxial to parallel plate transmission line transition means and parallel plate-type applicators in accordance with the invention for purposes of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention at defined in the appended claims.

What is claimed is:

1. Electromagnetic radiation apparatus, which comprises:
   (a) a plurality of applicators configured for irradiating living tissue and tissue simulating matter, each of said applicators having a radiation emitting surface; and, (b) conductive means fixed to each of the applicators adjacent said emitting surface, for providing radiation emitting extensions, said conductive means including deformable first and second flaps adapted to be positioned at least partially around the tissue or tissue simulating matter in substantial overlapping relationship with at least one of the flaps of adjacent ones of the applicators to thereby enclose portions of the tissue or tissue simulating matter within a cavity defined by the radiation emitting surfaces and overlapping flaps.

* * * * *